(12) United States Patent
Suprun et al.

(10) Patent No.: US 11,857,774 B2
(45) Date of Patent: Jan. 2, 2024

(54) INTRAVENOUS TUBING VENTING ASSEMBLY

(71) Applicant: UNIVERSITY OF FLORIDA RESEARCH FOUNDATION, INC., Gainesville, FL (US)

(72) Inventors: Andrey Suprun, Gainesville, FL (US); David Hutchinson, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 90 days.

(21) Appl. No.: 17/453,420

(22) Filed: Nov. 3, 2021

(65) Prior Publication Data
US 2022/0143327 A1    May 12, 2022

Related U.S. Application Data

(60) Provisional application No. 63/110,499, filed on Nov. 6, 2020.

(51) Int. Cl.
*A61M 5/36* (2006.01)
*A61M 5/168* (2006.01)

(52) U.S. Cl.
CPC .......... *A61M 5/36* (2013.01); *A61M 5/16813* (2013.01); *A61M 5/16881* (2013.01)

(58) Field of Classification Search
CPC . A61M 5/36; A61M 5/16813; A61M 5/16881
See application file for complete search history.

(56) References Cited

U.S. PATENT DOCUMENTS

| | | | |
|---|---|---|---|
| 3,631,654 A | | 1/1972 | Riely |
| 3,844,283 A | * | 10/1974 | Dabney ............... A61M 5/1411 |
| | | | 604/246 |
| 3,996,027 A | | 12/1976 | Schnell et al. |
| 4,900,308 A | * | 2/1990 | Verkaart ............... A61M 5/36 |
| | | | 604/126 |

(Continued)

FOREIGN PATENT DOCUMENTS

| WO | WO-1999/025422 A1 | 5/1999 |
|---|---|---|
| WO | WO-2012/033906 A2 | 3/2012 |

*Primary Examiner* — Dung T Ulsh
(74) *Attorney, Agent, or Firm* — ALSTON & BIRD LLP

(57) ABSTRACT

Provided herein is a method and apparatus for venting of intravenous tubing to remove air bubbles, and more particularly, to a venting valve that allows air bubbles to escape along a venting path while not permitting fluid passage through the venting path. An example air extraction device may include: a chamber; a fluid inlet to convey fluid from intravenous tubing into the chamber; a fluid outlet to convey fluid from the chamber to intravenous tubing for supplying to a patient; a top portion of the chamber; a branch tube extending from the top portion of the chamber, where the branch tube receives air from the fluid in the chamber; and a ball received within the chamber, where the ball is configured to rise with an influx of fluid to the chamber from the fluid inlet and to seal off the branch tube from the chamber in response to the fluid level rising to the top portion of the chamber.

15 Claims, 8 Drawing Sheets

(56) References Cited

U.S. PATENT DOCUMENTS

| | | | | |
|---|---|---|---|---|
| 6,013,061 | A | * | 1/2000 | Kelley ................. A61M 5/1411 604/126 |
| 6,193,689 | B1 | * | 2/2001 | Woodard .......... A61M 5/16881 604/122 |
| 6,481,455 | B2 | * | 11/2002 | Gustafson ............ B67D 1/1247 137/173 |
| 9,962,516 | B2 | | 5/2018 | Lampotang et al. |
| 2003/0040707 | A1 | * | 2/2003 | Kappel ................... A61M 5/36 604/129 |
| 2010/0204574 | A1 | * | 8/2010 | Duchon ................. A61B 6/481 700/282 |
| 2010/0280430 | A1 | * | 11/2010 | Caleffi .............. A61M 5/16854 604/65 |
| 2013/0172840 | A1 | | 7/2013 | Lampotang et al. |
| 2017/0113005 | A1 | * | 4/2017 | Lindner ............. A61M 5/31511 |
| 2018/0015251 | A1 | | 1/2018 | Lampotang et al. |

* cited by examiner

INTRAVENOUS TUBING VENTING ASSEMBLY

CROSS-REFERENCE TO RELATED APPLICATIONS

This application claims priority to U.S. Provisional Patent Application Ser. No. 63/110,499, filed on Nov. 6, 2020, the contents of which are hereby incorporated by reference in their entirety.

TECHNOLOGICAL FIELD

The present disclosure relates to venting of intravenous tubing to remove air bubbles, and more particularly, to a venting valve that allows air bubbles to escape along a venting path while not permitting fluid passage through the venting path.

BACKGROUND

In a healthcare context, fluids are conventionally introduced to a body by way of intravenous (IV) introduction from a fluid source, such as an IV bag or syringe, through IV tubing and into a patient through an IV catheter. While the goal is to convey fluids intravenously, air bubbles within the fluid can be problematic. Air bubbles in an intravenous delivery system may be conveyed to a patient and introduced into the patient's veins. An air bubble within the veins of a patient is known as an air embolism. Air embolisms can be deadly, particularly in the most vulnerable patients, such as premature infants. Current methods to avoid introducing air embolisms into a patient include sensors, such as within an IV pump, to detect air bubbles and to cease IV delivery when an air bubble is detected. To remove air bubbles, healthcare providers will often tap or flick intravenous tubing and hardware to move bubbles back up the IV tubing away from the patient. However, this method is rudimentary and often not entirely successful.

SUMMARY

An objective of this present disclosure is to provide a mechanism to remove air bubbles from intravenous tubing using an air extraction device. Embodiments provided herein include an air extraction device including: a chamber; a fluid inlet to convey fluid from intravenous tubing into the chamber; a fluid outlet to convey fluid from the chamber to intravenous tubing for supplying to a patient; a top portion of the chamber; a branch tube extending from the top portion of the chamber, where the branch tube receives air from the fluid in the chamber; and a ball received within the chamber, where the ball is configured to rise with an influx of fluid to the chamber from the fluid inlet and to seal off the branch tube from the chamber in response to the fluid level rising to the top portion of the chamber.

According to an example embodiment, the chamber is formed of a flexible material, where fluid is pumped through the chamber in response to a squeezing and releasing of the chamber. The chamber may be configured to release airlocks in the intravenous tubing leading to the fluid inlet in response to squeezing and releasing of the chamber. The fluid inlet may include a fluid inlet tube extending into the chamber, where the fluid outlet includes a fluid outlet tube extending into the chamber, and where the fluid inlet tube extends closer to the top portion of the chamber than the fluid outlet tube. The fluid inlet tube and the fluid outlet tube each extend into the chamber from a bottom of the chamber.

According to an example embodiment of the present disclosure, the ball is buoyant relative to the fluid. In response to the ball rising in the chamber and sealing off the branch tube from the chamber, fluid is precluded from flowing from the chamber into the branch tube. In response to air bubbles received into the chamber from the fluid inlet lowering the fluid level in the chamber, air is allowed to escape from the chamber into the branch tube. The branch tube may include a first end and a second end, where the first end of the branch tube is connected to the top portion of the chamber, and the second end of the branch tube is connected to an air reservoir.

Embodiments described herein may include a clamp configured to support the air extraction device, where the clamp secures the branch tube in a clip of the clamp. The clip of the clamp pinches and prevents the flow of air through the branch tube in response to the clamp not being secured to an object. The clip of the clamp opens and permits flow of air through the branch tube in response to the clamp being secured to an object.

Embodiments provided herein include an air extraction device for removing air from intravenous tubing, the device including: a chamber; a fluid inlet tube extending into the chamber to convey fluid from the intravenous tubing into the chamber; a fluid outlet tube extending into the chamber to convey fluid from the chamber to intravenous tubing for supplying to a patient, where the fluid inlet tube extends further into the cavity than the fluid outlet tube; a to portion of the chamber; a branch tube extending from the top portion of the chamber, where the branch tube receives air from the fluid in the chamber; and a ball received within the chamber, where the ball is configured to rise with an influx of fluid to the chamber from the fluid inlet and to seal off the branch tube from the chamber in response to a level of the fluid rising to the top portion of the chamber. The fluid conveyed from the intravenous tubing into the chamber includes air bubbles, and the fluid conveyed from the fluid chamber to the intravenous tubing for supplying to a patient does not include air bubbles. The air bubbles from the fluid conveyed from the intravenous tubing into the chamber exits the chamber through the branch tube.

BRIEF DESCRIPTION OF THE DRAWINGS

Some embodiments of this present disclosure may be further understood by the detailed descriptions and corresponding figures.

DETAILED DESCRIPTION

Figure 1:
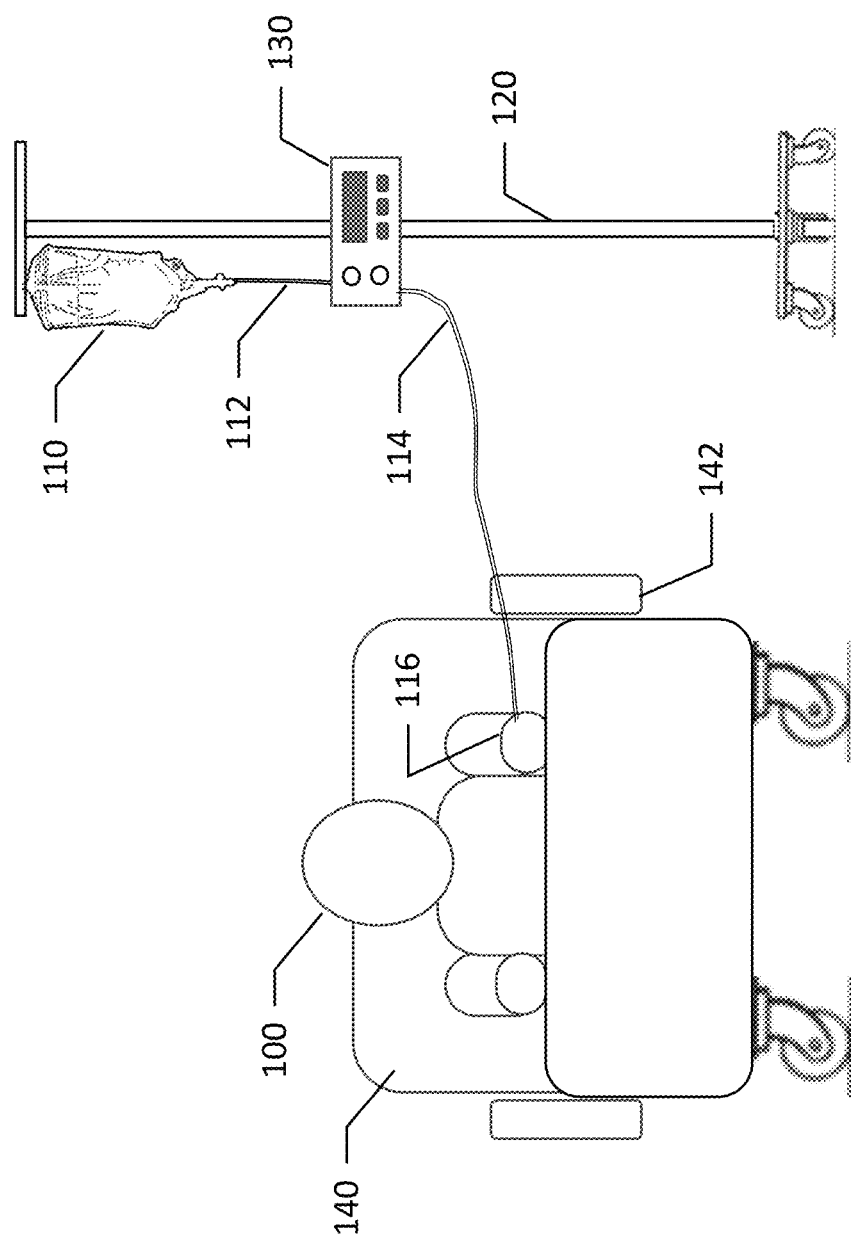
FIG. 1 illustrates a conventional IV arrangement for which a patient 100 receives a fluid intravenously from an IV bag suspended on a stand.

Some embodiments of the present invention will now be described more fully hereinafter with reference to the accompanying drawings, in which some, but not all, embodiments of the invention are shown. Indeed, various embodiments of the invention may be embodied in many different forms and should not be construed as limited to the embodiments set forth herein; rather, these embodiments are provided so that this disclosure will satisfy applicable legal requirements.

As noted above, fluid delivery to a patient intravenously through IV tubing can be challenging. Fluid delivery while removing air bubbles from the IV tubing is inefficient and sometimes ineffective. Embodiments described herein provide a device to remove air from IV tubing without interrupting fluid flow from a fluid source, such as an IV bag or syringe, to a patient. Embodiments may be employed in any setting where intravenous fluid introduction to a patient is performed using IV tubing.

According to an example embodiment provided herein, an air extraction device in-line with intravenous tubing to remove air from fluid flowing through the tubing and to carry the air to a reservoir or vent where the air is safely removed while enabling fluid flow through the IV tubing without air bubbles present after the in-line extraction device. The air extraction device described herein extracts air from IV tubing proximate a patient by establishing a branch from the IV tubing that provides a pathway for air removal from the fluid flow through the tubing. In order to prevent rapidly-infused medications from being forced into the branch tube, a ball valve is used. The fluid as described herein may be any fluid that is supplied to a patient via intravenous infusion. Fluid such as saline and/or liquid medications, for example. Fluid may also include blood infused intravenously from a reservoir or blood infused from a closed-loop dialysis system, for example.

Orientation of the air extraction device is imperative to function due to the air having a lower specific gravity than the fluid, where air rises relative to the fluid regardless of the gaseous make up of the air or the type of fluid being used in the IV. The term "air" is used herein to describe any gaseous substance found within the IV system. While atmospheric air is primarily Nitrogen and Oxygen, the air found in an intravenous system may be atmospheric air or may be air from within an IV bag, which may be anaerobic or have other chemical composition. Thus, the term "air" as used herein may be gases of any chemical composition.

Due to the air within IV tubing being lighter than the fluid flowing through the IV tubing, the orientation of the air extraction device is important for proper extraction of the air. The branch tube from which air is extracted from the IV tubing is raised relative to the IV tubing to promote air extraction. Embodiments provided herein further include a mechanism by which proper orientation of the air extraction device is maintained while also providing a mechanism to close the branch tube when the orientation of the air extraction device is improper.

FIG. 1 illustrates a conventional IV arrangement for which a patient 100 receives a fluid intravenously from an IV bag 110 suspended on a stand 120. As shown, the fluid from the IV bag 110 flows through a first tubing section 112 to an IV pump 130 and out of the IV pump along second tubing section 114 and into an arm of the patient 100 at IV site 116. The IV pump 130 is optional and not present in all situations in which a patient receives fluid intravenously. Optionally, the fluid may be fed through the IV tubing by gravity with the IV bag 110 suspended at sufficient height that the fluid flows through the tubing at a metered pace to the patient 100. The patient 100 of the illustrated embodiment is in a hospital bed 140 with bed rails 142. The hospital bed 140 is one conventional situation for a patient receiving intravenous fluids; however, it is not intended to be limiting.

Figure 2:
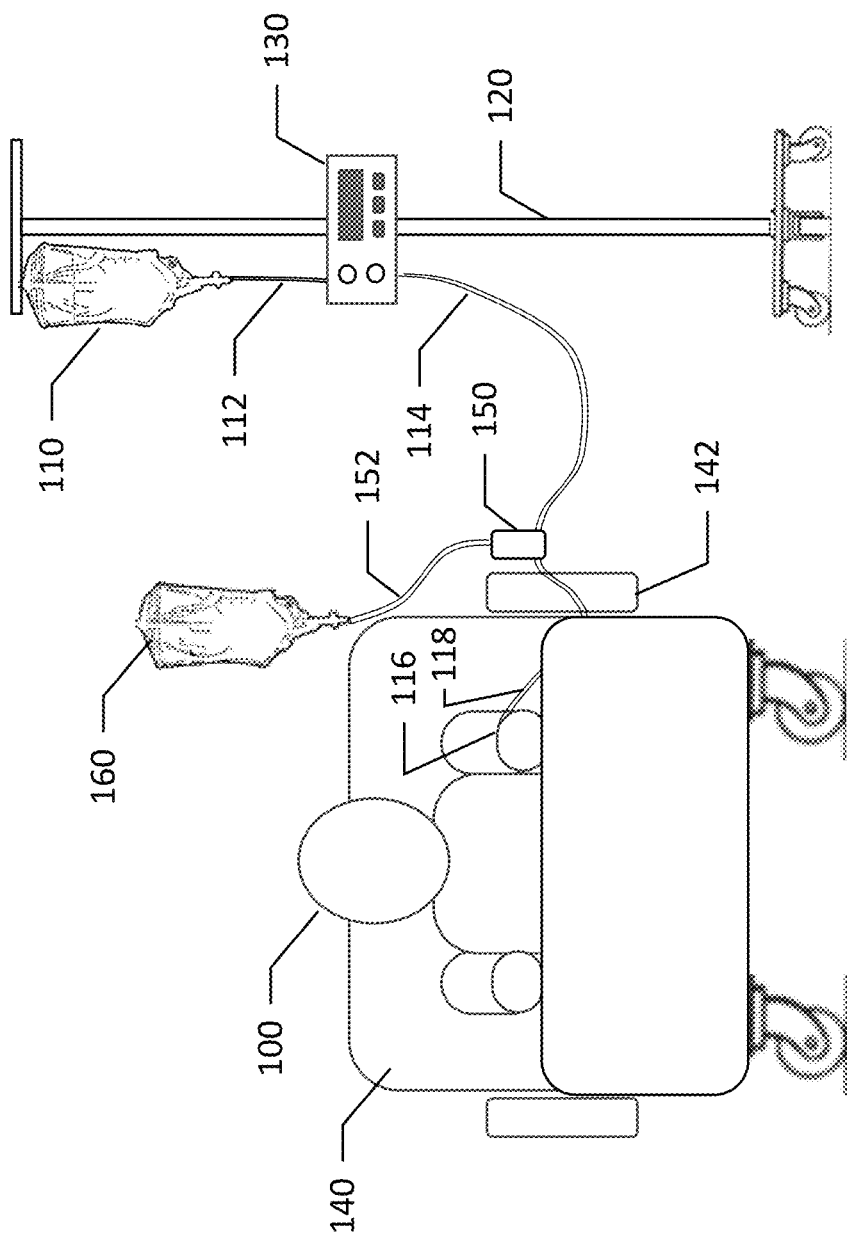
FIG. 2 illustrates an IV arrangement including an air extraction device 150 according to example embodiments of the present disclosure.

FIG. 2 illustrates an IV arrangement including an air extraction device 150 according to example embodiments of the present disclosure. The air extraction device 150 is positioned along the second tubing section 114 of the illustrated scenario, located close to the patient 100. The air extraction device 150 includes a branch tube 152 extending from the air extraction device 150, where the branch tube terminates at a reservoir 160 that may be present to collect the air extracted from the IV fluid. The reservoir 160 is optional and may be present to capture and monitor a volume of air extracted by the air extraction device 150. Further, the reservoir may function to maintain the IV fluid system, from the IV bag 110 to the patient 100, a closed system such that contaminants cannot be introduced to the system.

According to the illustrated embodiment of FIG. 2, fluid flows from the IV bag 110 through the first tubing section 112 to the IV pump 130, and along the second tubing section 114. While air has several ways of being introduced to the tubing, air may be introduced when medications are delivered to the IV tubing via a syringe connector. A syringe injecting medicine into the IV tubing may result in some amount of air introduced to the IV tubing. This may be due to air in the syringe, which may occur due to the method of filling the syringe, or the air bubbles may form through cavitation, for instance. Regardless, air bubbles traveling along the second tubing section 114 encounter the air extraction device 150. The air extraction device 150 separates the air bubbles from the fluid and expels the air along the branch tube 152 to the reservoir 160 while the IV fluid continues along the patient-side IV tubing 118 to the patient IV site 116.

Figure 3:
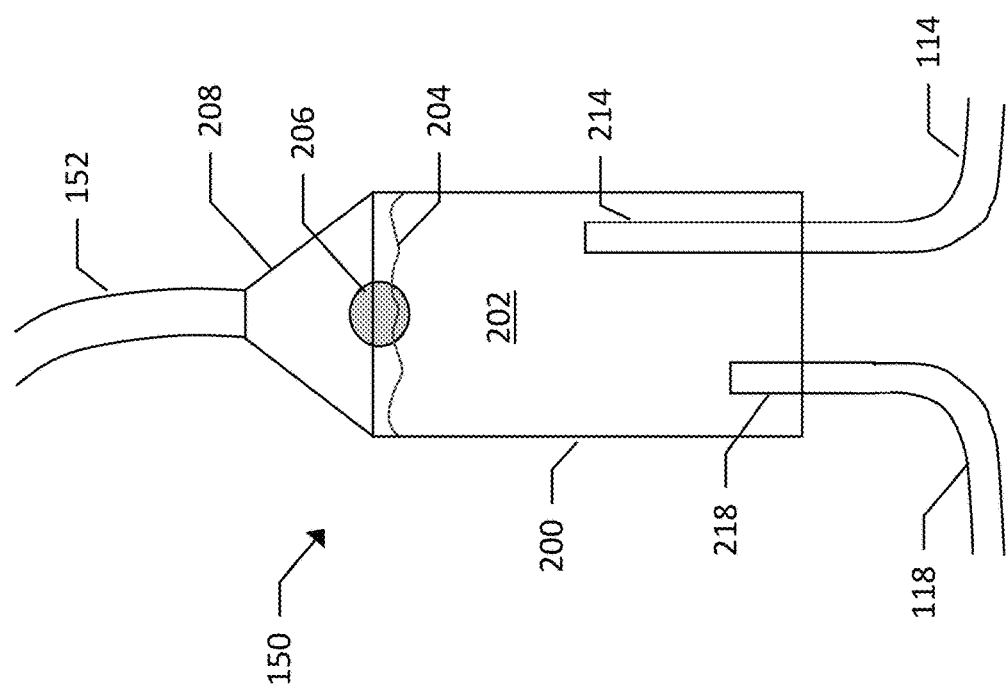
FIG. 3 illustrates a diagram of features of the air extraction device of FIG. 2 shown in greater detail according to example embodiments of the present disclosure.

FIG. 3 illustrates a diagram of features of the air extraction device 150 of FIG. 2 shown in greater detail. As shown, the air extraction device 150 includes a fluid inlet 214 where the second tubing section 114 enters chamber 200. The fluid 202 in the chamber flows out through fluid outlet 218 to patient-side IV tubing 118. The fluid 202 fills the chamber 200 to a fluid level 204. A ball 206 floats at the fluid level 204. The ball 206 density may be chosen based on the type of fluid that is to be intravenously provided to a patient; however, the density is generally such that the ball remains buoyant on the fluid while only partially submerged below the fluid level 204. A less dense ball 206 may be more responsive to fluctuations in fluid; however, a less dense ball may also be subject to premature closing of the ball valve while a more dense ball, while still remaining buoyant in the fluid, may respond more slowly. A more dense ball 206 may permit fluid flow into the branch tube 152 in response to a sudden influx of fluid into the chamber 200.

The chamber 200 includes at a top portion 208 that narrows to meet the branch tube 152. The narrowing top portion 208 may be frustoconical or frusto-pyramidal whereby as the fluid level 204 of the fluid 202 rises, the ball 206 floats up. As the fluid level 204 continues to rise, the ball 206 is guided by the narrowing top portion 208 to close off or seal the branch tube 152. This ball valve functionality prevents or reduces the likelihood of fluid flow into the branch tube 152, and allows the fluid 202 to continue to flow from the chamber 200 through fluid outlet 218 along the patient-side IV tubing 118. As will be described further below, this ball valve functionality does not enable air flow through the air extraction device 150 to the patient despite being able to close off the branch tube 152 in response to a high fluid level 204.

Figure 4:
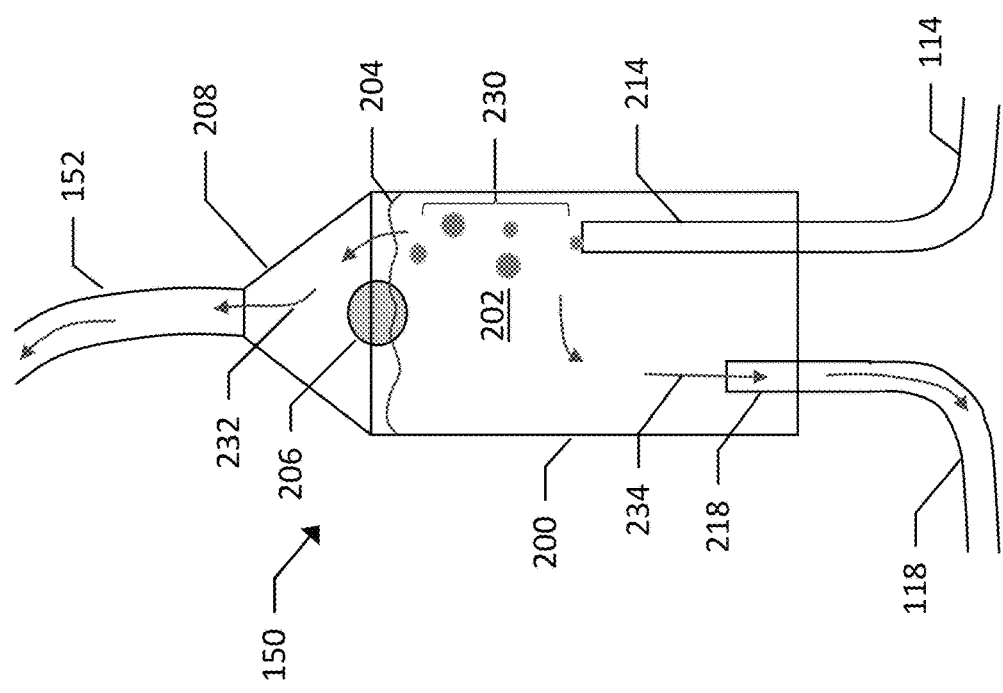
FIG. 4 illustrates the air extraction device of FIG. 3 including the extraction of air bubbles from the fluid according to an example embodiment of the present disclosure.
Figure 5:
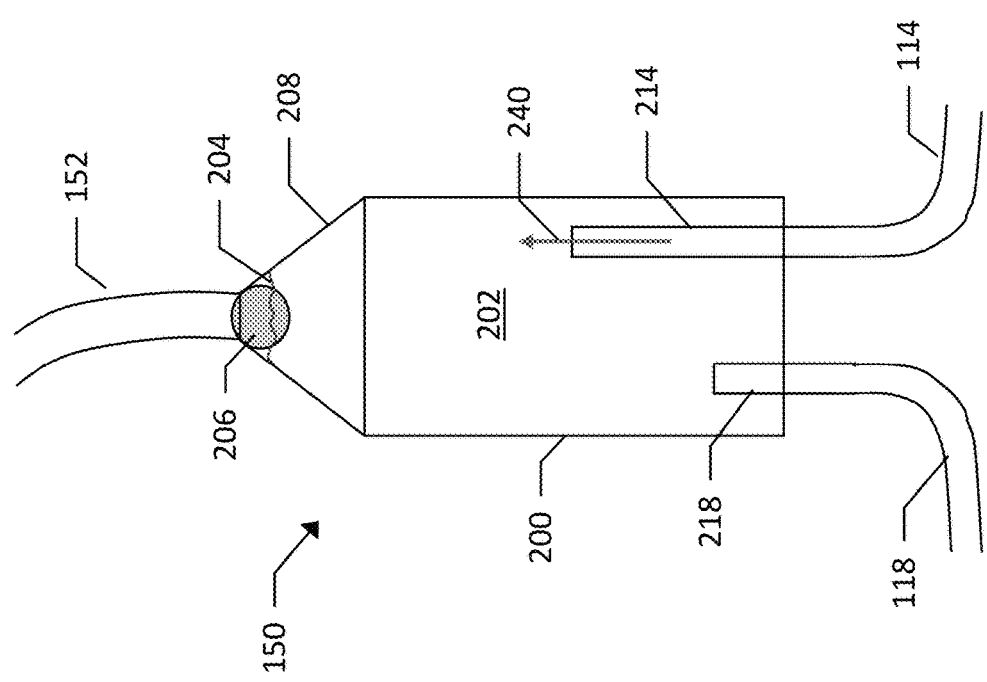
FIG. 5 illustrates the air extraction device of FIG. 3 including a fluid level rise sufficient for the ball to seal the branch tube from the chamber according to an example embodiment of the present disclosure.

FIG. 4 illustrates the air extraction device during operation, while fluid 202 is flowing in through the fluid inlet 214 and out through fluid outlet 218 of the chamber 200. As shown, when fluid is received at the chamber 200 with air bubbles 230, the air bubbles 230 float up within the chamber 200 due to the top portion 208 being elevated relative to the inlet 214 and the air being lighter than the fluid 202. The air bubbles 230 crest the fluid level 204 and the air is carried up the branch tube 152 as illustrated by arrows 232. Maintaining fluid level 204 results in any air introduced into the chamber 200 further pushing air in the chamber up through the branch tube 152. Fluid 202, with air bubbles 230 having escaped, then flows through fluid outlet 218 to the patient-side IV tubing 118 as shown by arrows 234 for delivery to the patient 100.

The illustration of FIG. 4 demonstrates the primary functional purpose of the air extraction device 150 whereby air is separated from the fluid 202 and allowed to escape from the IV tubing by way of the branch tube 152 without disrupting the fluid flow from the IV bag 110 to the patient 100. This extraction of the air from the fluid reduces the chances of an air embolism thereby improving the safety of intravenous fluid infusion. The fluid inlet 214 is elevated within the chamber 200 relative to the fluid outlet 218 to further discourage air from exiting through the fluid outlet 218 as the air accumulates in the top portion 208 of the chamber as described above.

In some situations, fluid may flow rapidly through the IV fluid system illustrated in FIG. 2. Such situations include where rapid rehydration or medication absorption is needed by a patient. In these situations, it remains imperative to extract air from the fluid flow while also precluding fluid from escaping from the system through the branch tube 152. FIG. 4 illustrates an example embodiment in which fluid is flowing rapidly through fluid inlet 214 into the chamber 200. When this begins to happen, the fluid level 204 will rise quickly. When the fluid level 204 rises, the ball 206 is carried by the fluid into the top portion 208 of the air extraction device 150 where the ball 206 plugs the exit of the chamber to the branch tube 152. The fluid 202 is thus precluded from flowing through the branch tube 152 and away from the patient. The fluid is instead forced to exit the chamber 200 through the fluid outlet 218 along the patient-side IV tubing 118 to the patient 100 for delivery of the rapidly flowing fluid.

Figure 6:
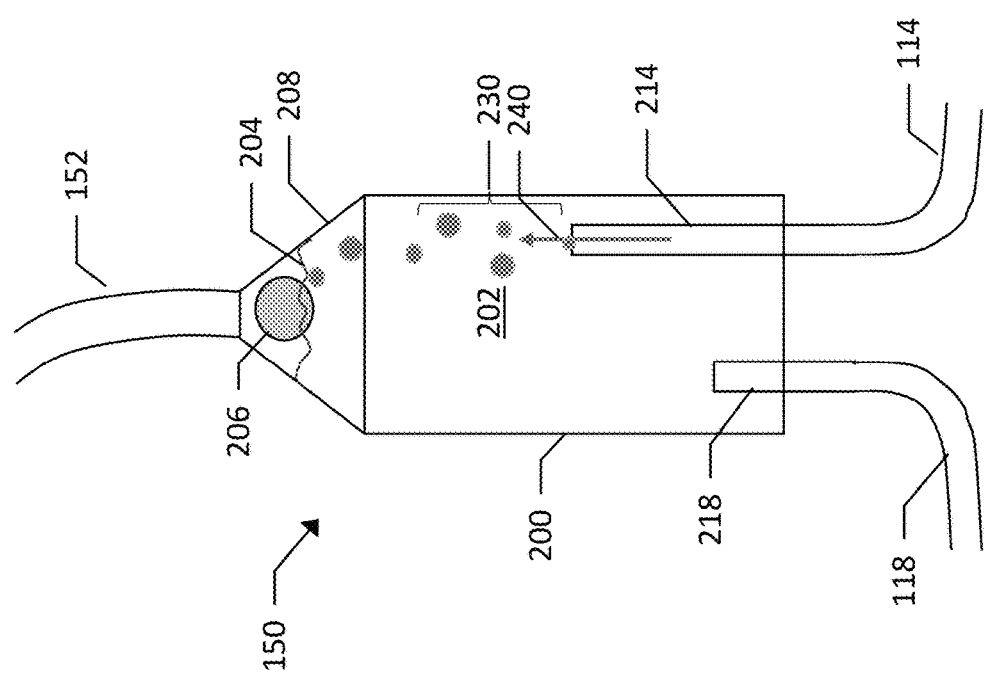
FIG. 6 illustrates the air extraction device of FIG. 3 including the extraction of air bubbles from the fluid according to an example embodiment of the present disclosure.

While the branch tube 152 is plugged during rapid fluid flow, the air extraction device 150 continues to function. FIG. 6 illustrates that if air bubbles are received while fluid is flowing rapidly through the air extraction device 150, the bubbles will rise in the chamber 200 and accumulate in the top portion 108 of the chamber around the ball 206. When a sufficient amount of air bubbles have been received, the fluid level 204 descends and opens a pathway for the air to escape through the branch tube 152. During rapid fluid flow, the fluid level 204 may rise to close the branch tube 152 with ball 206, and periodically sufficient air bubbles may be received in the chamber to lower the fluid level 204 sufficiently to enable air to escape through the branch tube 152 whereupon the fluid level 204 may rise again to close the branch tube 152 with the ball 206. Thus, even during rapid fluid flow, the air extraction device 150 continues to function to extract air from the fluid and expel the air along the branch tube 152.

Figure 7:
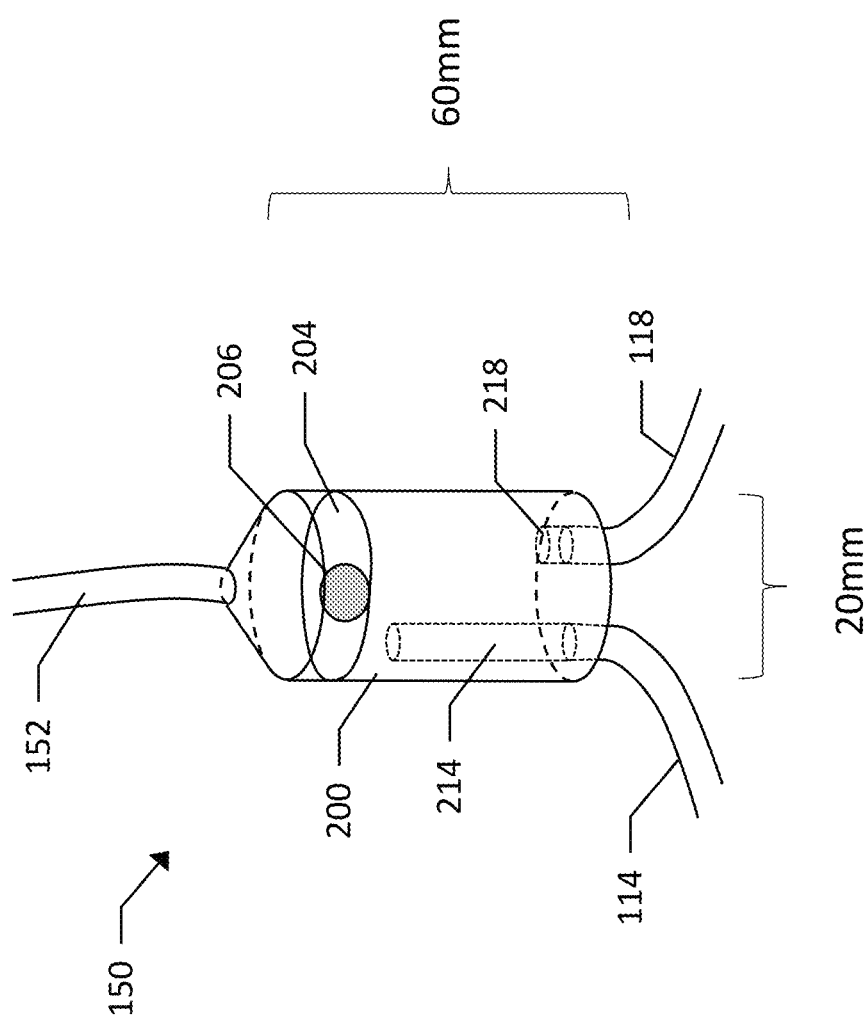
FIG. 7 illustrates another example embodiment of an air extraction device according to an example embodiment of the present disclosure.

FIG. 7 illustrates a perspective view of the air extraction device with dimensions of an example embodiment. As shown, an air extraction device 150 of an example embodiment may have a width of 20 millimeters and a height of 60 millimeters. The shape of the chamber 200 may be cylindrical with a frustoconical top portion 208. Optionally, the chamber 200 may be of a flexible membrane with no structural shape, whereby the chamber 200 is relatively flat when empty, but inflates with fluid as intravenous fluid enters the chamber through fluid inlet 214. Even if the chamber 200 includes a structural shape, the chamber may be constructed of a flexible material, such as the same material as the intravenous tubing or of a silicone, for example. Embodiments in which the chamber is flexible provide an advantage that the chamber 200 can be used as a pump to remove airlocks from the intravenous tubing.

The flexible nature of the chamber 200 of some embodiments is counterintuitive to a chamber that includes a ball check valve as disclosed herein. This is due to a conventional ball check valve having a rigid enclosure to enable the ball to move consistently and repeatably. However, applicant has developed a chamber 200 that can be flexible while including a ball 206 of a check valve to prevent fluid flow through the branch tube 152. According to example embodiments described herein, the ball 206 only needs to close the branch tube 152 in response to the chamber filling with fluid. When the chamber 200 fills with fluid, the chamber volume becomes substantially the maximum volume possible for the chamber, thus establishing the shape defined by the flexible material in an expanded position. As the ball 206 is only employed for function when the chamber 200 is filled, the chamber is substantially the same repeatable, and defined shape whenever the ball 206 is used. Thus, while the chamber may be of a flexible and pliable material that can be used for pumping of fluid as detailed herein, the ball 206 valve sealing retains full functionality despite the flexible nature of the chamber.

Airlocks occur in intravenous tubing where air bubbles exist in the tubing and preclude fluid flow or the flow of the air bubbles through the tubing. Historically these airlocks have been removed by tapping or flicking the IV tubing to drive the air up the tubing to an IV bag. However, embodiments described herein can pump fluid through the chamber 200 while simultaneously expelling air through the branch tube 152 by squeezing the chamber. This pumping action may draw the airlock into the chamber 200 through the fluid inlet 214 where the air passes through the branch tube while the fluid continues to flow through the fluid outlet 218. This pumping action does not preclude functionality of the air extraction device 150 and instead benefits the air extraction device by providing additional functionality of being a fluid/air pump that pulls fluid and air through the inlet 214 and expels the fluid and air through different outlets while preventing air from flowing to a patient.

In order for the air extraction device 150 to properly function, the chamber 200 should be maintained at the height of the patient or lower such that air does not enter the patient-side IV tubing 118 from the chamber. The arrangement of the air extraction device 150 below the IV bag 110 enables flow of fluid to the air extraction device 150 by gravity feeding or by IV pump 130. Further, maintaining the reservoir at the height of the patient's IV site 116 or lower does not allow air to enter the patient-side IV tubing 118. To help maintain this arrangement, embodiments described herein may employ a clip from which the air extraction device 150 is hung. The clamp may include a normally-closed clip that closes down on the branch tube 152 to preclude flow of any fluid or air through the branch tube 152 while the clamp is not attached to an object.

Figure 8:
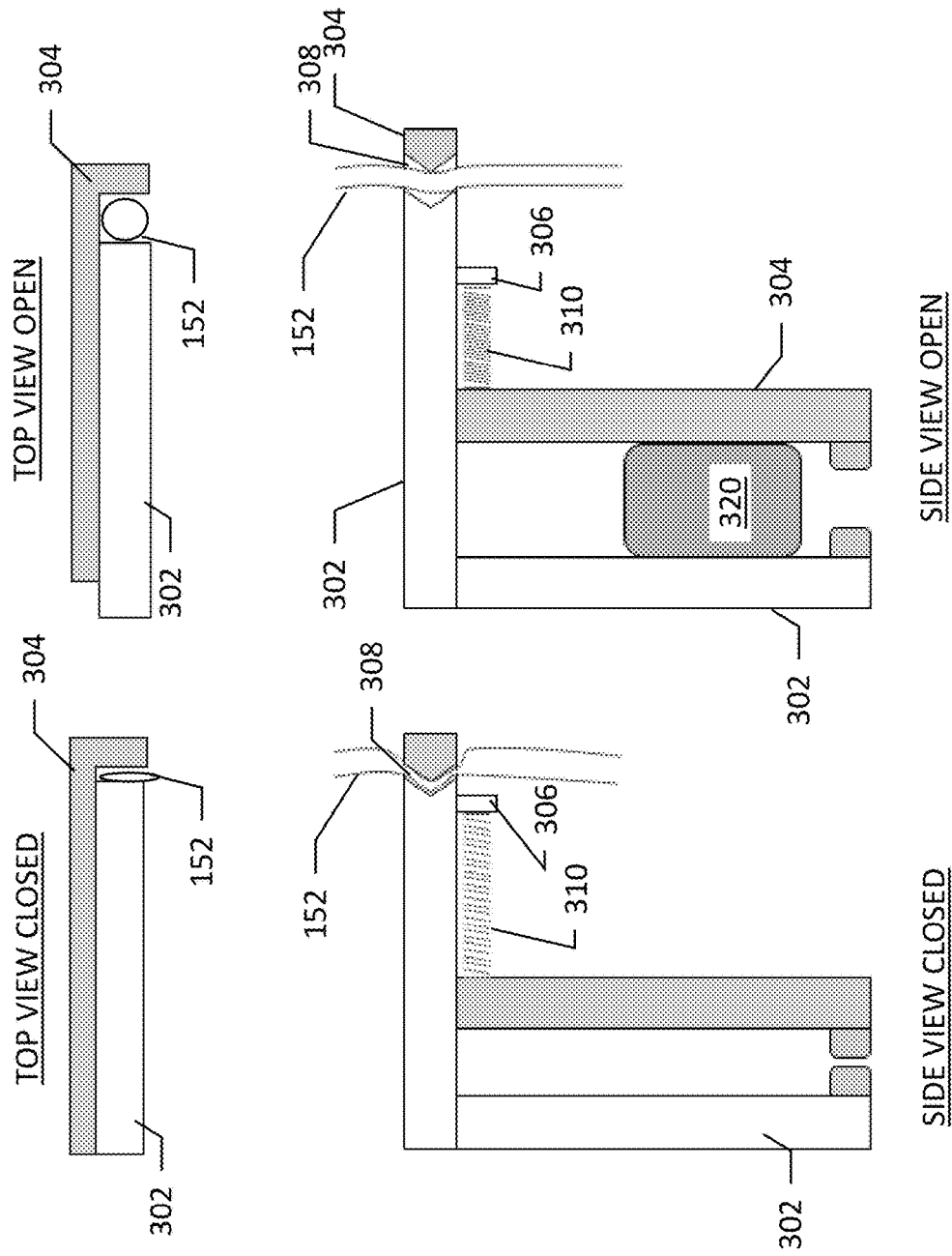
FIG. 8 illustrates a clamp of an air extraction device according to an example embodiment of the present disclosure.

FIG. 8 illustrates an example clamp 300 that may be used to close the branch tube 152 while the clamp is not attached to an object, and to open the branch tube 152 when attached to an object, such as a bed rail 320 of a hospital bed. The clamp 300 of the illustrated embodiment includes two primary components of a first part 302 and a second part 304. In the closed position, whereby the branch tube 152 is closed, a spring biases the second part 304 toward the first part 302, closing a clip 308 formed by the two parts. This pinches the branch tube 152 as shown in the top view closed illustration. When the clamp is attached to an object such as a bed rail 320 of a hospital bed, the first part 302 is pushed away from the second part 304 compressing the spring 310 against element 306 while opening the clip 308. Thus, when the clamp is attached to an object, as to be done by a nurse or attending caregiver, the air extraction device 150 is ensured to be in the correct orientation with the branch tube 152 extending upward from the chamber 200. If the clamp were not clamped to an object, as shown in the "closed" position of FIG. 8, the orientation of the air extraction device 150 is not ensured, such that the branch tube 152 is closed.

Embodiments of the air extraction device described herein may be positioned anywhere between the IV fluid source (e.g., the IV bag 110) and the patient 100 provided the air extraction device 150 is positioned at an appropriate elevation with respect to the fluid source and the patient. However, according to embodiments in which the air extraction device 150 is located downstream of an IV pump 130 as shown in FIG. 2, the air extraction device may substantially eliminate any air bubbles from the IV tubing. IV pumps 130 may include air bubble detection means to detect when air exists in the IV tubing. When air is detected in the IV tubing, the IV pump 130 may cease operation until the issue is rectified by a medical professional, and/or the air detection means may cause an alarm to sound to alert an attending medical professional of the detected air in the IV tubing. When employing the air extraction device 150 as described herein, the air bubble detection means of an IV pump may be turned off since air bubbles passing through the IV pump will be mitigated downstream by the air extraction device. The turning off of the air bubble detection means and associated alarm reduces the time an attending medical professional has to spend dealing with alarms, both false alarms and legitimate alarms, such that the efficiency and efficacy of the medical professionals can be improved.

Any modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An air extraction device for removing air from intravenous (IV) tubing, the device comprising:
   a chamber;
   a fluid inlet tube to convey fluid from intravenous tubing into the chamber;
   a fluid outlet tube to convey fluid from the chamber to intravenous tubing for supplying to a patient; wherein the fluid inlet tube extends further into the chamber than the fluid outlet tube;
   a top portion of the chamber;
   a branch tube extending from the top portion of the chamber, wherein the branch tube receives air from the fluid in the chamber; and
   a ball received within the chamber, wherein the ball is configured to rise with an influx of fluid to the chamber from the fluid inlet tube and to seal off the branch tube from the chamber in response to a level of the fluid level rising to the top portion of the chamber, wherein the ball within the chamber functions as a check valve to prevent fluid flow through the branch tube and to allow air to flow through the branch tube.

2. The air extraction device of claim 1, wherein the chamber is formed of a flexible material, wherein fluid is pumped through the chamber in response to a squeezing and releasing of the chamber.

3. The air extraction device of claim 1, wherein the chamber is formed of a flexible material, and wherein the chamber is configured to release airlocks in the intravenous tubing leading to the fluid inlet tube in response to squeezing and releasing of the chamber.

4. The air extraction device of claim 1, wherein the fluid inlet tube extends closer to the top portion of the chamber than the fluid outlet tube.

5. The air extraction device of claim 4, wherein the fluid inlet tube and the fluid outlet tube each extend into the chamber from a bottom of the chamber.

6. The air extraction device of claim 1, wherein the ball is buoyant relative to the fluid.

7. The air extraction device of claim 1, wherein in response to the ball rising in the chamber and sealing off the branch tube from the chamber, the device precludes fluid flow from the chamber into the branch tube.

8. The air extraction device of claim 7, wherein in response to air bubbles received into the chamber from the fluid inlet tube lowering the level of the fluid in the chamber, the device allows air from the air bubbles to pass through the branch tube.

9. The air extraction device of claim 1, wherein the branch tube has a first end and a second end, wherein the first end of the branch tube is connected to the top portion of the chamber, and wherein the second end of the branch tube is connected to an air reservoir.

10. The air extraction device of claim 1, further comprising a clamp, wherein the air extraction device is supported by the clamp, and wherein the clamp secures the branch tube in a clip.

11. The air extraction device of claim 10, wherein the clip of the clamp pinches and prevents flow of air through the branch tube in response to the clamp not being secured to an object.

12. The air extraction device of claim 11, wherein the clip of the clamp opens and permits flow of air through the branch tube in response to the clamp being secured to an object.

13. An air extraction device for removing air from intravenous (IV) tubing, the device comprising:
 a chamber;
 a fluid inlet tube extending into the chamber to convey fluid from intravenous tubing into the chamber;
 a fluid outlet tube extending into the chamber to convey the fluid from the chamber to intravenous tubing for supplying to a patient;
 a top portion of the chamber;
 a branch tube extending from the top portion of the chamber, wherein the branch tube receives air from the fluid in the chamber;
 an air reservoir to collect air extracted from the fluid and provide a volume measure of the air received from the fluid in the chamber; and
 a ball received within the chamber, wherein the ball is configured to rise with an influx of fluid to the chamber from the fluid inlet and to seal off the branch tube from the chamber in response to a level of the fluid level rising to the top portion of the chamber, wherein the ball within the chamber functions as a check valve to prevent fluid flow through the branch tube and to allow air to flow through the branch tube.

14. The air extraction device of claim 13, wherein the fluid conveyed from the intravenous tubing into the chamber comprises air bubbles, wherein the fluid conveyed from the chamber to intravenous tubing for supplying to a patient does not include air bubbles.

15. The air extraction device of claim 14, wherein the air bubbles from the fluid conveyed from the intravenous tubing into the chamber exit the chamber through the branch tube.

* * * * *